United States Patent
Wink

(10) Patent No.: US 10,137,038 B2
(45) Date of Patent: Nov. 27, 2018

(54) STERILE ADHESIVE BANDAGE CONTAINING A POCKET

(71) Applicant: Doreen Musto Wink, Rockville, MD (US)

(72) Inventor: Doreen Musto Wink, Rockville, MD (US)

(*) Notice: Subject to any disclaimer, the term of this patent is extended or adjusted under 35 U.S.C. 154(b) by 353 days.

(21) Appl. No.: 15/138,351

(22) Filed: Apr. 26, 2016

(65) Prior Publication Data

US 2017/0143554 A1 May 25, 2017

Related U.S. Application Data

(60) Provisional application No. 62/258,594, filed on Nov. 23, 2015.

(51) Int. Cl.
*A61F 13/00* (2006.01)
*A61F 13/02* (2006.01)

(52) U.S. Cl.
CPC .. *A61F 13/00085* (2013.01); *A61F 13/00063* (2013.01); *A61F 13/025* (2013.01); *A61F 13/0206* (2013.01); *A61F 2013/00251* (2013.01)

(58) Field of Classification Search
CPC ............ A61F 13/00085; A61F 13/0206; A61F 13/025; A61F 13/00063; A61F 2013/00251; A61F 2013/00089; A61F 15/005; A61F 13/0259
See application file for complete search history.

(56) References Cited

U.S. PATENT DOCUMENTS

| | | | | |
|---|---|---|---|---|
| 4,641,643 A | * | 2/1987 | Greer | A61F 13/0246 128/888 |
| 5,086,763 A | * | 2/1992 | Hathman | A61F 13/0246 128/887 |
| 5,449,340 A | * | 9/1995 | Tollini | A61M 25/02 128/888 |
| 5,702,356 A | * | 12/1997 | Hathman | A61F 13/0206 128/888 |
| 2002/0019602 A1 | * | 2/2002 | Geng | A61F 13/00063 602/42 |
| 2011/0092874 A1 | * | 4/2011 | Baschnagel | A61F 13/0203 602/54 |
| 2014/0358058 A1 | * | 12/2014 | Nelson | A61F 13/00063 602/48 |

* cited by examiner

*Primary Examiner* — Tarla R Patel
(74) *Attorney, Agent, or Firm* — Dunlap Bennett & Ludwig PLLC; Brendan E. Squire

(57) ABSTRACT

An adhesive bandage comprising a base portion having a gauze portion to contact a wound and an adhesive portion, and the base portion defining a pocket adapted for storing the gauze portion, and allowing inspection and replacement thereof without having to remove the entire bandage.

8 Claims, 3 Drawing Sheets

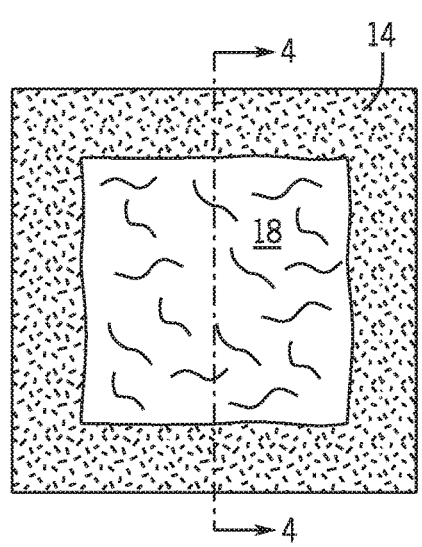
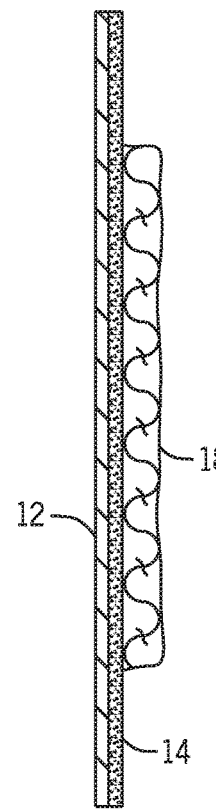
FIG. 3
FIG. 4
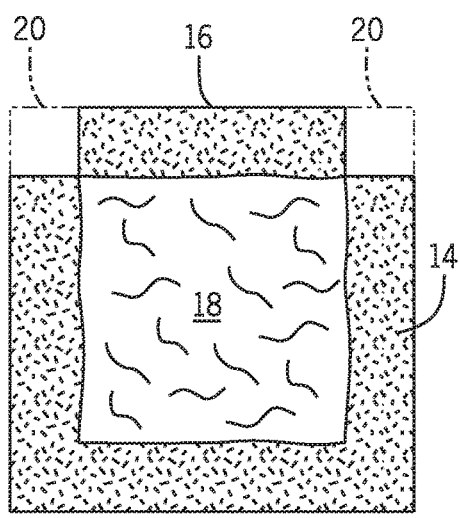
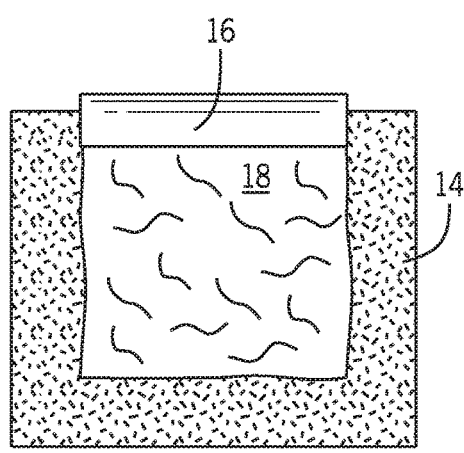
FIG. 5
FIG. 6

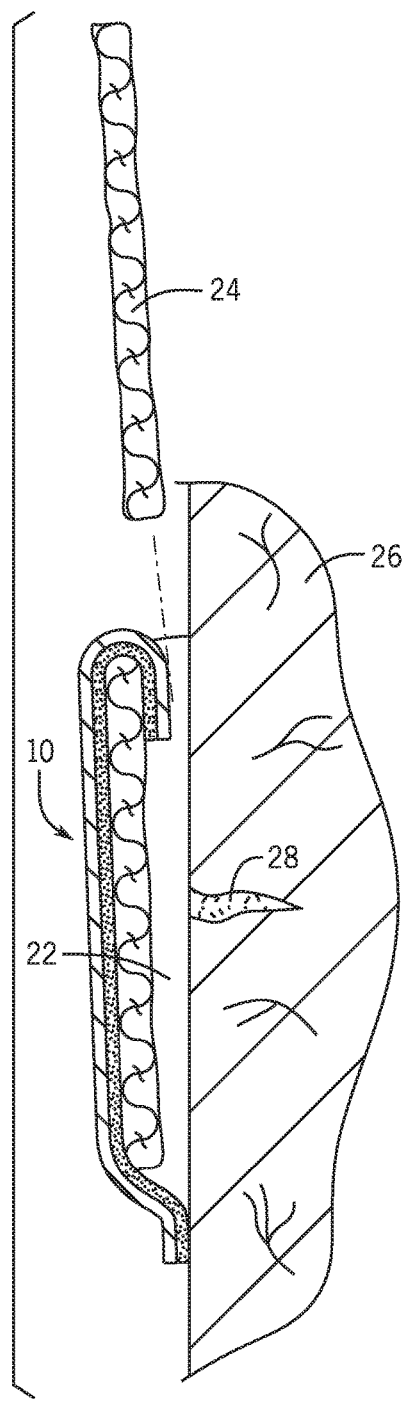
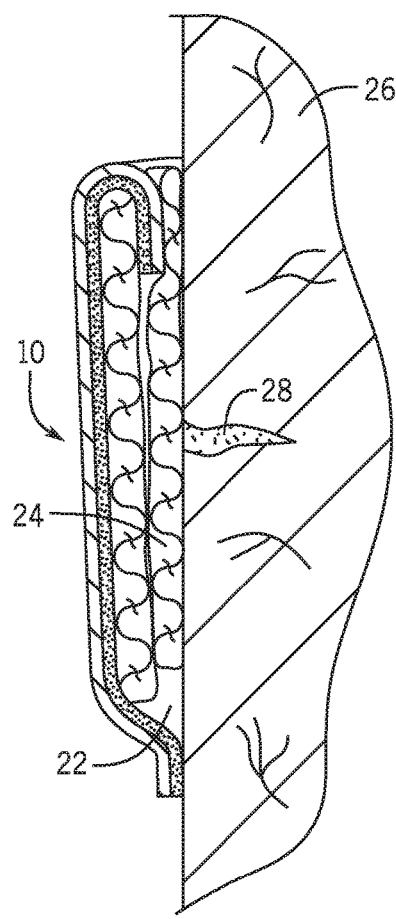
FIG. 7
FIG. 8

STERILE ADHESIVE BANDAGE CONTAINING A POCKET

CROSS-REFERENCE TO RELATED APPLICATION

This application claims the benefit of priority of U.S. provisional application No. 62/258,594, filed Nov. 23, 2015, the contents of which are herein incorporated by reference.

BACKGROUND OF THE INVENTION

The present invention relates to sterile adhesive bandage products and, more particularly, to adhesive bandages comprising a pocket for positioning gauze pads on a wound.

Present day wound care requires the application of adhesive bandages thereto and their frequent replacement. Each such replacement requires the often painful and harmful ripping-off of the old bandage from the patient's skin, and with the attendant risk of exposing the wound to pathogens.

Currently, therefore, there is a need for a more user-friendly wound care system that significantly reduces the chances of infection of the wound.

SUMMARY OF THE INVENTION

One embodiment of the present invention provides an adhesive bandage comprising a pocket in which sterile, wound-contacting gauze may be positioned, thereby allowing inspection and replacement thereof without having to remove the entire bandage, thus avoiding the above-noted disadvantages associated with conventional adhesive bandages.

These and other features, aspects and advantages of the present invention will become better understood with reference to the following drawings, description and claims.

BRIEF DESCRIPTION OF THE DRAWINGS

FIG. 3 is front elevation view of the first step in making the invention.

FIG. 4 is a cross-sectional view taken on line 4-4 of FIG. 3.

FIG. 5 is a front elevation view of the second step in making the invention.

FIG. 6 is a front elevation view of the third step in making the invention.

FIG. 7 is an exploded side cross-sectional view showing the invention in use.

FIG. 8 is a side cross-sectional view showing the invention in use.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Figure 1:
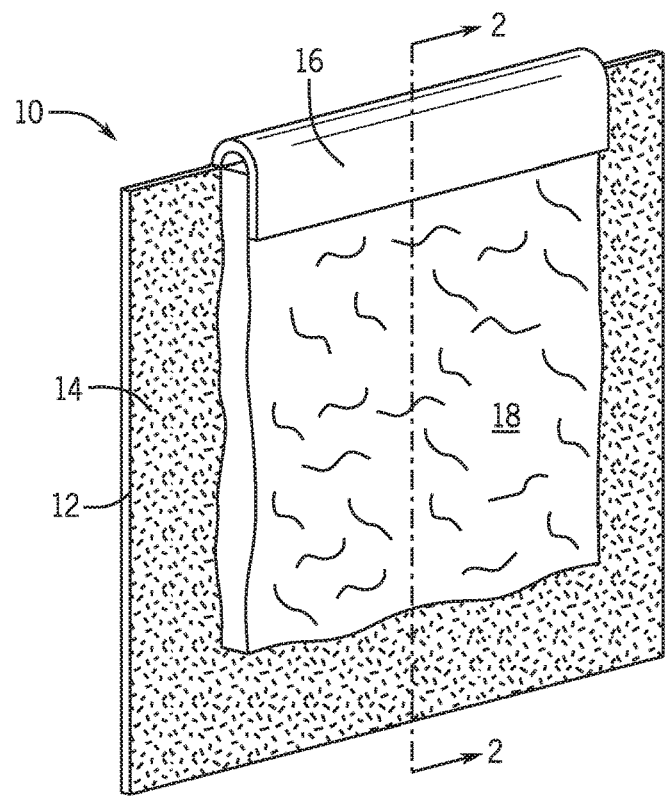
FIG. 1 is a perspective view of the invention.
Figure 2:
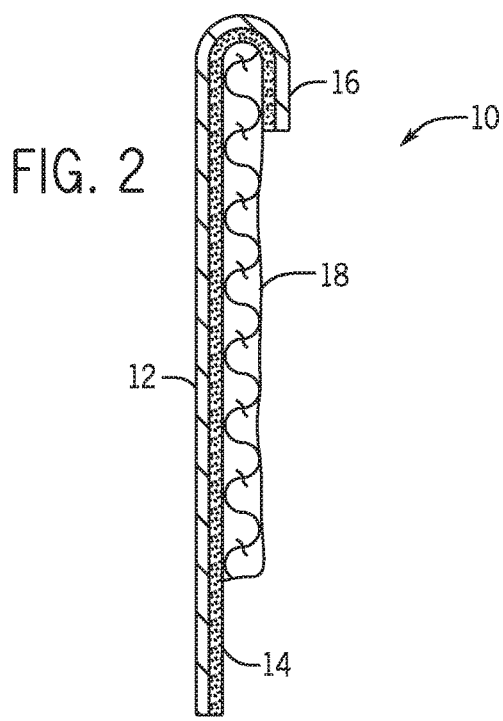
FIG. 2 is a cross-sectional view taken on line 2-2 of FIG. 1.

A preferred embodiment of the invention is depicted in FIGS. 1 through 8, wherein:

10 is the adhesive bandage of the invention,
12 is the base,
14 is the adhesive,
16 is the flap,
18 is the permanent gauze pad,
20 are the clipped off corners,
22 is the pocket,
24 is a second gauze pad,
26 is the flesh, and
28 is the wound.

The adhesive bandage 10 of the invention comprises base 12 coated with adhesive 14. Flap 16 is positioned on the base 12, preferably with adhesive, to form pocket 22 in which a first permanent gauze pad 18 and, optimally, a second gauze pad 24 are housed. Corners 20 may be clipped off so that the remainder of the top may be folded over to secure the permanent gauze pad 18 and to prevent its unraveling, and to facilitate adherence and ultimate removal of the bandage from the wound 28 in the flesh 26.

The bandage of the invention renders wound care easier and less painful. It saves time, effort and money in that it is not necessary to remove the bandage to inspect the wound or replace the gauze dressing contacting the wound. Therefore, the inspection and dressing replacement processes are less painful to the patient since the portion of the bandage adhered to the skin does not need to be removed, thereby being more convenient to the medical staff and/or patient.

In addition, the bandage of the invention maintains an environment of sterility around the wound which is unmatched by those currently available. Thus, the bandage of the invention significantly reduces the chances of infection of the wound under care by opportune pathogens.

Preferably, the bandage 10 is adhered to the skin 26 such that the pocket 22 is at least one to two inches above the wound 28 as preferred or needed. Pocket 22 is filled with gauze layers 18 and, optimally, 24, which contact the wound. The gauze dressing may be inspected and changed as often as needed with no need to de-adhere the adhesive layer 14 from the skin 26.

The sterile adhesive 'pocket' (22) may be of any convenient size; e.g., 4"×4", 6"×6" and/or shapes: square, horseshoe, rectangle or round, provided an opening is provided therein for the insertion of gauzes, dressing, other medical material, or any of the other elements listed above.

The sterile pocket 22 is, in addition, preferably of a size to hold items other than gauze dressings such as, for example, thermometers, small medical devices, small antibacterial items, and social media devices so that the patient or health care provider can access them while bed ridden. They may be pleated so they can hold more, or bulkier gauzes, sponges, materials, products that are deemed necessary by medical staff and/or patient. The pockets may also be adorned with designs to render the bandage product pleasing to the eye of the adult or child patient.

It will be understood by those skilled in the art that the elements of the adhesive bandage of the invention may be constructed from any of the materials conventionally employed.

The base (12) material may comprise, for example, porous or perforated films, plastics, textiles, nonwoven materials, impregnated composites thereof, and combinations thereof. The bandage substrate can be an elastic material, such as a woven material containing elastomeric fibers, or a laminate of one or more bandage layers with one or more elastomeric layers.

The gauze pads (18) and (24) may consist of, for example, a cellulosic material, such as gauze, an airlaid web, a wetlaid web, a hydroentangled web containing pulp and synthetic fibers, a coform web, and the like. In other embodiments, the base (12) may comprise a bonded carded web, a foam, a film, a woven fabric, a knitted fabric, a hydroentangled web containing synthetic fibers only, a meltblown web, a spunbond web, and laminates thereof.

Any of the commonly available suitable adhesives may be employed for the adhesive layer (14), such as, for example, any hypoallergenic, skin-friendly adhesive known in the art, such as rubbery adhesives, acrylic adhesives, polyurethane adhesives, silicone adhesives, and block copolymer adhesives and those described in U.S. Pat. Nos. 4,147,831, 4,551,490, and EPO 361 72261, EP 1008330A2, and WO 00/12038.

EXAMPLE

A 6"×6" square of sterile vinyl adhesive (clear or flesh colored) is positioned with adhesive side up. A 4"×4" square of gauze is placed and secured on the center of the vinyl adhesive, leaving an approximately one inch border on all sides. At the top of the 6"×6" adhesive square, 1" squares of adhesive layer is cut off of the corners on the top left and right sides of the adhesive square. The adhesive layer that is left over in the middle (at top of adhesive square) is folded down, covering the top of the gauze (this seals the gauze at the top so that it does not start to unravel).

A separate adhesive 'tab' (not shown) may be provided at the opening of the pocket to facilitate its closing, if needed or desired. It will be understood by those skilled in the art that the adhesive bandage of the invention may be provided with any of the accoutrements conventionally employed in the medical care field such as, for example, a color strip to alert the nurse/caregiver/patient of when it is best to change the dressing in the pocket.

The pocket may be constructed of optically clear material to facilitate inspection of the dressing contained therein.

It will be apparent to those skilled in the art that the wound-contacting gauze pads may be impregnated with therapeutic agents, bioactive agents, antibiotics, bactericides, fungicides, drugs, growth factors, peptides, proteins, enzymes, emollients, antiseptics, anti-oxidants, wetting agents, and mixtures thereof. For example, the gauze pads (18 and 24) may be treated with antiseptic benzalkonium chloride and an antibiotic mixture of polymixin B-sulfate and bacitracin-zinc, or any of those antibacterial agents disclosed in U.S. Pat. Nos. 4,192,299, 4,147,775, 3,419,006, 3,328,259, and 2,510,993.

Finally, a preferred embodiment of the invention comprises a bandage as described above wherein the pocket is sufficiently large to allow significant air circulation which, upon contacting the wound area, aids in the healing process.

It should be understood, of course, that the foregoing relates to exemplary embodiments of the invention and that modifications may be made without departing from the spirit and scope of the invention as set forth in the following claims.

What is claimed is:

1. An adhesive bandage comprising a base portion having at least one gauze portion adapted to contact a wound in a skin surface and an adhesive portion; the adhesive portion having an adhesive on a first surface of the base portion adapted to adhere to skin around three sides of and peripheral to the wound; the base portion defining a pocket adapted for storing the at least one gauze portion, wherein the pocket comprises a folded over flap of the base portion and a side opening of the pocket allowing inspection and replacement of the at least one gauze portion without having to remove the entire bandage.

2. A method for changing the wound-contacting gauze portion associated with the adhesive bandage of claim 1, the method comprising: adhering the adhesive bandage to the skin of a patient around the three sides and peripheral to the wound, with a gauze portion contacting the wound in or on a skin surface; subsequent to the adhering, removing the wound-contacting gauze portion; and replacing it with a second gauze portion over the wound in the skin while the adhesive bandage remains adhered to the skin.

3. The adhesive bandage of claim 1, wherein the gauze portion is impregnated with a member selected from the group consisting of therapeutic agents, bioactive agents, antibiotics, bactericides, fungicides, drugs, growth factors, peptides, proteins, enzymes, emollients, antiseptics, antioxidants, wetting agents, and mixtures thereof.

4. The adhesive bandage of claim 1, wherein said base portion comprises a member selected from the group consisting of porous or perforated films, plastics, textiles, nonwoven materials, elastic materials, woven materials containing elastomeric fibers, or and combinations thereof.

5. The adhesive bandage of claim 1, wherein said gauze portion comprises a member selected from the group consisting of an air laid web, a wetland web, a hydro entangled web containing pulp and synthetic fibers, a coform web, and combinations thereof.

6. The adhesive bandage of claim 1, wherein said adhesive comprises a skin-friendly adhesive selected from the group consisting of rubbery adhesives, acrylic adhesives, polyurethane adhesives, silicone adhesives, block copolymer adhesives and mixtures thereof.

7. The adhesive bandage of claim 1, wherein the base portion is pleated.

8. The adhesive bandage of claim 1, the base portion further comprising,
a flap extending along the side opening of the pocket, an adhesive applied to the flap for securement of the flap to a skin facing surface of the gauze portion.

* * * * *